(12) United States Patent
Zhang (10) Patent No.: US 9,775,347 B2
(45) Date of Patent: Oct. 3, 2017

(54) METHODS TO CONVERT LIGNIN TO PHENOLIC AND CARBOXYLATE COMPOUNDS

(71) Applicant: WASHINGTON STATE UNIVERSITY RESEARCH FOUNDATION, Pullman, WA (US)

(72) Inventor: Xiao Zhang, Richland, WA (US)

(73) Assignee: Washington State University, Pullman, WA (US)

(*) Notice: Subject to any disclaimer, the term of this patent is extended or adjusted under 35 U.S.C. 154(b) by 0 days.

(21) Appl. No.: 14/898,442

(22) PCT Filed: Jun. 14, 2013

(86) PCT No.: PCT/US2013/045927
§ 371 (c)(1),
(2) Date: Dec. 14, 2015

(87) PCT Pub. No.: WO2014/200509
PCT Pub. Date: Dec. 18, 2014

(65) Prior Publication Data
US 2016/0135452 A1 May 19, 2016

(51) Int. Cl.
| | |
|---|---|
| *A01N 31/08* | (2006.01) |
| *A01N 35/04* | (2006.01) |
| *A01N 31/14* | (2006.01) |
| *A01N 37/02* | (2006.01) |
| *A01N 37/40* | (2006.01) |
| *A01N 61/00* | (2006.01) |
| *C07C 27/00* | (2006.01) |
| *C07C 45/59* | (2006.01) |
| *C07C 51/31* | (2006.01) |
| *C10G 3/00* | (2006.01) |

(52) U.S. Cl.
CPC ............ *A01N 37/02* (2013.01); *A01N 31/08* (2013.01); *A01N 31/14* (2013.01); *A01N 35/04* (2013.01); *A01N 37/40* (2013.01); *A01N 61/00* (2013.01); *C07C 27/00* (2013.01); *C07C 45/59* (2013.01); *C07C 51/31* (2013.01); *C10G 3/00* (2013.01); *C10G 3/50* (2013.01); *Y02P 30/20* (2015.11)

(58) Field of Classification Search
CPC ........ A01N 31/08; A01N 31/14; A01N 35/04; A01N 37/02; A01N 37/40; A01N 61/00; C07C 27/00; C07C 45/59; C07C 51/31; C10G 3/00; C10G 3/50; Y02P 30/20
See application file for complete search history.

(56) References Cited

U.S. PATENT DOCUMENTS

| | | |
|---|---|---|
| 2,069,185 A | 1/1937 | Hibbert |
| 3,663,712 A | 5/1972 | Von Schmeling |
| 5,959,167 A | 9/1999 | Shabtai et al. |
| 6,214,976 B1 | 4/2001 | Watanabe et al. |
| 8,114,644 B1 | 2/2012 | Yang |
| 2011/0275869 A1 | 11/2011 | Prochazka et al. |
| 2012/0107886 A1 | 5/2012 | Albizati et al. |

FOREIGN PATENT DOCUMENTS

| | | |
|---|---|---|
| WO | 2010141499 A2 | 12/2010 |
| WO | 2012036884 A2 | 3/2012 |
| WO | 2013015895 A2 | 1/2013 |

OTHER PUBLICATIONS

Albrecht, An Investigation of the physical-chemical mechanism of selective delignification of wood with peracetic acid, Dissertation Lawrence University, pp. 1-207, 1971.*
Albrecht et al., An investigation of the physical-chemical mechanism of selective delignification of wood with peracetic acid, Dissertation Lawrence University, pp. 1-207 (Jun. 1971).
Holladay et al., Top Value-Added Chemicals from Biomass, Results of Screening for Potential Candidates from Biorefinery Lignin vol. II, pp. 1-79 (Oct. 2007).
International Search Report and Written Opinion for International Application No. PCT/US13/45927 mailed Jan. 8, 2014.
Pitz et al., Development of an Experimental Database and Kinetic Models for Surrogate Gasoline Fuels. SAE International Paper 2007-01-0175, pp. 1-24 (Apr. 16, 2007).
Thring et al., Hydrocracking of solvolysis lignin in a batch reactor, Fuel, vol. 75, Issue. 7, pp. 795-800 (May 1996).

* cited by examiner

*Primary Examiner* — Paul A Zucker
*Assistant Examiner* — Mark Luderer
(74) *Attorney, Agent, or Firm* — Pepper Hamilton LLP (57) ABSTRACT

A method of converting lignin to phenolic compounds and dicarboxylates in high yield is described. The method involves the use of peroxy acids to react with lignin at a moderated treatment conditions. The peroxy acids can be used along or in combination of other catalysts that have the capability to lower the molecular weight of lignin. A phenolic compounds yield is achieved (>60%) and these phenolic compounds represents high value precursors for various applications include but not limited to antioxidants, health improvement agents, anticorrosive agents, liquid fuel components and performance enhancing agents, resin and adhesives. Dicarboxylic acids can be used for polymer applications or hydrodeoxygenation to hydrocarbon fuel.

16 Claims, 6 Drawing Sheets

METHODS TO CONVERT LIGNIN TO PHENOLIC AND CARBOXYLATE COMPOUNDS

CLAIM OF PRIORITY

This application is a U.S. national stage filing under 35 U.S.C. §371 of International Application No. PCT/US2013/45927 filed on Jun. 14, 2013 entitled "METHODS TO CONVERT LIGNIN TO PHENOLIC AND CARBOXYLATE COMPOUNDS," which is incorporated herein by reference in its entirety.

BACKGROUND

Lignin is a major constituent of plant biomass and represents the second largest organic polymer on our planet. A large quantity of lignin is generated from pulp and paper-making processes. The upcoming biomass biorefinery industry will bring in an enormous amount of lignin. However, despite significant efforts in the past few decades, the commercial lignin market has stagnated at about one million tons per year. Catalytic degradation of biorefinery lignin to low molecular weight phenolic compounds is an area which has not been well studied.

It is clear that there is a lack of efficient method to convert polymeric lignin at a moderate condition to phenolic compounds in high yield. Most of the processes either lack the selectivity to obtain target products in high yield or require high temperature and high pressure conditions.

SUMMARY

Lignin is the largest source of renewable material with an aromatic skeleton. Depolymerizing lignin to low molecular weight aromatic and phenolic compounds offers an attractive opportunity to produce a range of potential high value products/chemicals. Lignin can be chemically and/or biologically depolymerized into smaller molecular weight phenolic compounds. Phenolic compounds have been applied as anti-oxidants to reduce the amount of dissolved oxygen in biofuel, and hence to prevent metal corrosion. Another area permitting large quantity application of lignin derived phenolic compounds is in biofuels. Conventional fossil fuels contain a significant amount of aromatics (up to 50% by volume) either derived from petroleum or blended as additives. Besides providing energy value, fuel aromatics also function as antioxidants and anti-corrosive agents. Most biofuel products (e.g., biodiesel from plant oil, bio-alcohols from ligno-cellulosic biomass) are expected to have low aromatics content, due to either the nature of the feedstock or process configurations. Supplementing lignin derived phenolic compounds to biofuels will not only increase the energy content but also improve the quality of biofuels.

Disclosed are processes to produce both phenolic and dicarboxylate compounds comprising oxidative depolymerizing a lignin thereof with a peroxy acid at a temperature of not greater than about 160° C. to give a mixture of dicarboxylic acid compounds and a mixture of phenolic compounds. The mixture of dicarboxylic acid compounds may be formed in at least about 10% total weight yield, and the mixture of phenolic compounds may be at least about 28% total weight yield, wherein the total weight yield is calculated from the lignin on a contained lignin basis. Processes disclosed may further comprise formation of one or more organic solvents or combination thereof in at least about 5% total weight yield. In some embodiments, the oxidative depolymerizing is at a temperature of not less than about 60° C. to not greater than about 90° C. for about 10 minutes to about 3 hours. In other embodiments, the reaction is at least 3 hours. Shorter times favor the formation of phenolic products, while longer reaction time favors formation of dicarboxylic acids. Peak yields of phenolic products may be obtained at about 1-2 hours.

Also disclosed are antimicrobial mixtures of compounds comprising benzoic acid, vanillin, vanillic acid, gallic acid, and at least one substituted aryl ether. In addition, antibacterial agents may be produced by providing a lignin; decomposing the lignin with a peroxy acid for at least ten minutes and not greater than 3 hours at a temperature of not less than 40° C. to not greater than 120° C. to give a decomposition product; and extracting decomposition product with an organic solvent to give a solution of the antibacterial agent. Further, an antibacterial agent may be produced by providing a lignin; decomposing the lignin with a peroxy acid to give a decomposition product; partitioning the decomposition product between aqueous phase and an organic phase; and concentrating the antibacterial agent.

The use of synthetic antibiotics in animals is a controversial practice in animal agriculture. Overuse of antibiotics has led to antimicrobial resistant microbes. There is significant movement toward prohibiting and reduce the use of synthetic antibacterial agents. Biobased antibacterial derived from lignin has a potential to replace synthetic antibiotics. Further, adhesives derived from biomass lignin have the potential to be cost competitive and to reduce petroleum consumption.

DESCRIPTION OF DRAWINGS

For a fuller understanding of the nature and advantages of the present technologies, reference should be had to the following detailed description taken in connection with the accompanying drawings, in which.

DETAILED DESCRIPTION

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art. Any methods and materials similar or equivalent to those described herein can be used in the practice or testing of embodiments disclosed.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

The term "alkyl" or "alkyl group" refers to a branched or unbranched hydrocarbon or group of 1 to 20 carbon atoms, such as but not limited to methyl, ethyl, n-propyl, isopropyl, n-butyl, isobutyl, t-butyl, octyl, decyl, tetradecyl, hexadecyl, eicosyl, tetracosyl and the like. "Cycloalkyl" or "cycloalkyl groups" are branched or unbranched hydrocarbons in which all or some of the carbons are arranged in a ring, such as but not limited to cyclopentyl, cyclohexyl, methylcyclohexyl and the like. The term "lower alkyl" includes an alkyl group of 1 to 10 carbon atoms.

The term "aryl" or "aryl group" refers to monovalent aromatic hydrocarbon radicals or groups consisting of one or more fused rings in which at least one ring is aromatic in nature. Aryls may include but are not limited to phenyl, naphthyl, biphenyl ring systems and the like. The aryl group may be unsubstituted or substituted with a variety of substituents including, but not limited to, alkyl, alkenyl, halide, benzylic, alkyl or aromatic ether, nitro, cyano and the like and combinations thereof.

"Substituent" refers to a molecular group that replaces a hydrogen in a compound and may include, but are not limited to, trifluoromethyl, nitro, cyano, $C_1$-$C_{20}$ alkyl, aromatic or aryl, halide (F, Cl, Br, I), $C_1$-$C_{20}$ alkyl ether, benzyl halide, benzyl ether, aromatic or aryl ether, hydroxy, alkoxy, amino, alkylamino (—NHR'), dialkylamino (—NR'R") or other groups which do not interfere with the formation of the diaryl alkylphosphonate.

Methods to convert lignin to phenolic compounds in high yield at moderate conditions are described herein. The produced phenolics compounds can be applied as antioxidant, adhesive, animal feed fuel additives, or any other known applications of phenolic compounds. Methods are also described to further convert phenolic compounds to aromatic fuel components.

Peroxy acids, such as peracetic acid or persulfuric acid, are a group of selective delignification agents. Oxygen insertion is a characteristic step in peroxy acids catalyzed reaction with lignin. Due to their high oxidation potential, peroxy acids depolymerization of lignin can be performed at moderate conditions to minimize aromatic ring opening reactions.

Process embodiments include methods to produce both phenolic and dicarboxylate compounds comprising oxidative depolymerizing a lignin thereof with a peroxy acid at a temperature of not greater than about 160° C. to give a mixture of dicarboxylic acid compounds and a mixture of phenolic compounds. In some embodiments, the mixture of dicarboxylic acid compounds is in at least about 10% total weight yield, and the mixture of phenolic compounds is in at least about 28% total weight yield, wherein total weight yield is calculated from the lignin on a contained lignin basis. The solutions may include one or more organic solvents or combination thereof in at least about 5% total weight yield.

Various embodiments of the method include substantially separating one or more dicarboxylic acid compounds or combination thereof from the mixture of phenolic compounds; reducing at least one of the dicarboxylic acid compounds to a saturated dicarboxylic acid; recovering one or more dicarboxylic acids or combination thereof in at least about 10% total weight yield.

Various other embodiments include substantially separating one or more dicarboxylic acid compounds or combination thereof from the mixture of phenolic compounds; esterifying at least one of the dicarboxylic acid compounds to a dicarboxylate ester; recovering one or more dicarboxylate esters or combination thereof in at least about 10% total weight yield.

Figure 2:
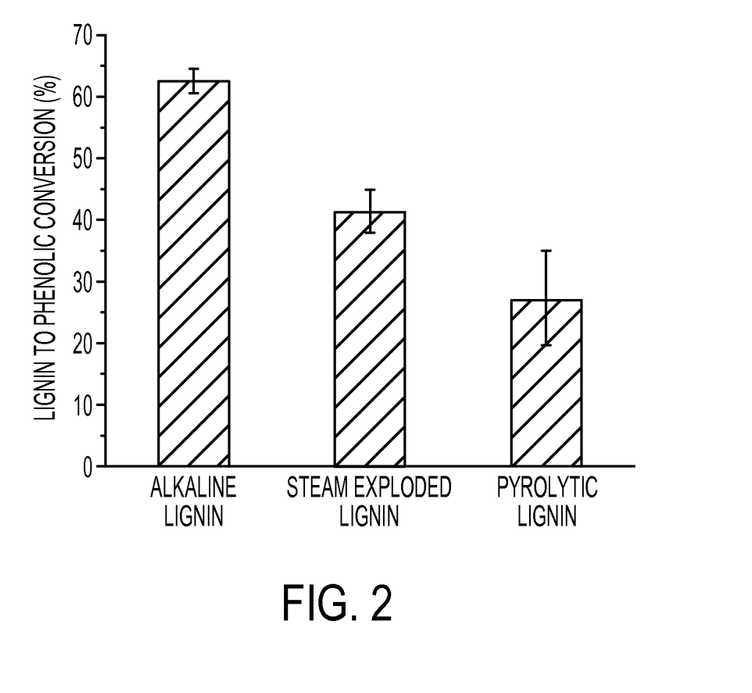
FIG. 2: Phenolic compound yield obtained from different lignin feedstock.

The lignin may be any available lignin. The lignin may be an alkaline lignin, a steam exploded lignin, or a steam exploded lignin having an enzyme treatment, a pyrolytic lignin, or combination thereof. FIG. 2 shows alkaline lignin has surprisingly higher yields of phenolic conversion as compared to steam exploded lignin. Steam exploded lignin gave surprisingly higher yields than pyrolytic lignins.

The Klason lignin assay may be used to determine lignin content of a sample. Klason lignin is obtained. In the Klason lignin assay method, polysaccharides are hydrolyzed by treating wood with sulfuric acid to provide water-soluble sugars, and the lignin is recovered as an insoluble residue. The Klason content of the lignin used, expressed as a weight percentage, is about 50% by weight to about 100% by weight or a range within that range. As used herein, the term "percent (or %) by weight" or "weight percentage", when applied to the lignin content of treated pulp, means weight percentage relative to the dry weight of the treated pulp. Lignin content is measured by a sugar content assay based on Technical Association of Pulp and Paper Industries (TAPPI) standard method T249 cm-00 and lignin content is estimated from the solid residue after filtration of sugar solution from hydrolyzed samples. In a summary of the method, samples are hydrolyzed with sulfuric acid using a two-step technique. The precipitate is isolated and dried. In embodiments, the Klason lignin assay is at least 50%, at least 60%, at least 70%, at least 75%, at least 80%, at least 85%, at least 90%, at least 95%, at least 99%, or greater. "Contained lignin basis" are calculated using a Klason lignin assay result on the dried the lignin utilized. Yields and total weight yields are calculated from the dried lignin utilized using a Klason lignin assay result.

The oxidative depolymerization is performed at moderate temperatures. The oxidative depolymerization can be performed at a reaction temperature of not less than about 5° C. to not greater than about 160° C. In some embodiments, the reaction is performed at a temperature of about 40° C. to not greater than about 120° C. In other embodiments, the reaction is performed at a temperature of about 60° C. to not greater than about 90° C. In certain other embodiments, the reaction is performed at about 30° C., about 40° C., about 50° C., about 60° C., about 70° C., about 80° C., about 90° C., about 100° C., about 120° C., about 140° C., about 160° C., or a range between any two of the specified temperatures. Specific embodiments have ranges of about 25-120° C., about 40-120° C., about 40-90° C., about 50-80° C., and about 60-90° C.

Figure 1:
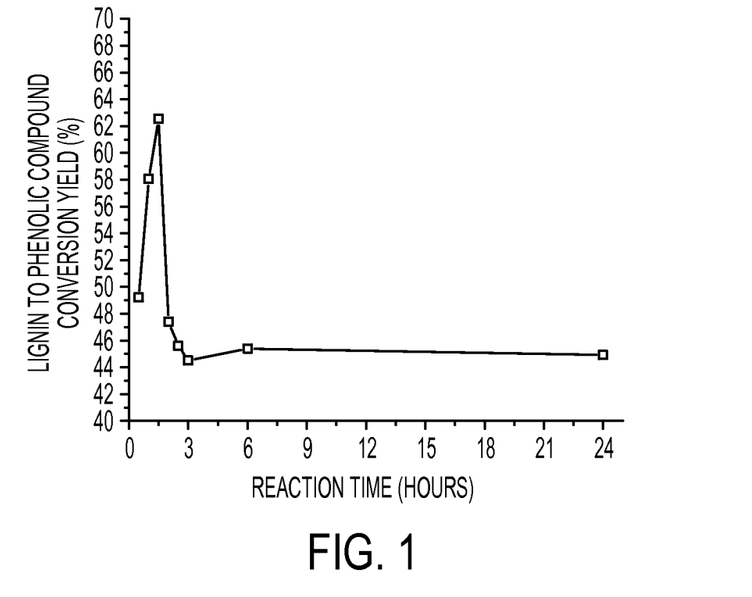
FIG. 1: Lignin to phenolic compounds conversion yield during peracetic acid treatment.

In some reactions, the reaction is performed for about 10 minutes to about 3 hours. In other reactions, the minimum temperature of the temperature range is held for at least three hours. As a non-limiting example, an embodiment has the oxidative depolymerization performed at not less than 60° C. for 10 minutes to three hours, with an upper temperature of not more than 90° C. In another embodiment, the depolymerization is performed at not less than 60° C. for about 150 minutes, with an upper temperature of not more than 90° C. In yet another embodiment, the oxidative depolymerization is performed at not less than 60° C. for at least three hours. FIG. 1 shows an unexpected result wherein a maximum phenolic compounds yield was reached at about 1.5 hours of reaction at about 60° C. Longer reaction times favored dicarboxylic acid formation.

The peroxy acid may include any organic peroxy acid. In some embodiments, the peroxy acid includes peracetic acid, performic acid, or combinations thereof. In other embodiments, the peroxy acid is a peroxyaryloic acid. In certain embodiments, the peroxyaryloic acid is a peroxybenzoic acid. In still other embodiments, the peroxy acid is a m-chloroperoxybenzoic acid (MCPBA). The peroxy acid may be generated in situ from an organic acid and hydrogen peroxide. The formation of a peroxy acid may be catalyzed by an organic catalyst or inorganic catalyst in the presence of hydrogen peroxide.

When the oxidizing agent includes a peroxy acid prepared in situ, it may be prepared in any manner, such as by combining a peroxide and an acid. Any peroxide or combination of peroxides that can provide a peroxy acid be used, such as hydrogen peroxide, for example, aqueous hydrogen peroxide. Any acid or combination of acids that can provide a peroxy acid can be used, such as formic acid, or acetic acid, for example, aqueous solutions of formic and/or acetic acid. Performic acid may be obtained, for example, by combining hydrogen peroxide and formic acid. Peracetic acid may be obtained by combining hydrogen peroxide with acetic acid.

The peroxy acid may include a peroxysulfuric acid. The peroxy acid may include peroxymonosulfuric acid, peroxydisulfuric acid, peroxysulfonic acid, or a mixture thereof. Most of peroxy acids can be decomposed to simple acid, oxygen and water. Using peroxy acids for lignin conversion to phenolic compounds provides a green process for lignin conversion.

The peroxy acid may be added or prepared in a quantity dependent upon the weight of the contained lignin. In some embodiments, the quantity of added or in situ prepared peroxy acid is 0.01-0.5:1 weight:weight ratio. Thus, in that embodiment for each 100 grams of lignin, the lignin would be added or prepared one to fifty grams of peroxy acid. In other embodiments, the quantity of peroxy acid is 0.001-0.5:1 w/w %, is 0.001-0.25:1 w/w %, 0.01-0.5:1 w/w %, 0.01-0.25:1 w/w %, 0.01-0.15:1 w/w %, or 0.05-0.25:1 w/w %. In situ preparation may be achieved by a hydrogen peroxide or an alkali metal peroxide.

The depolymerizing may be performed in an aqueous medium, a non-aqueous medium, or a biphasic mixture of an aqueous medium and a non-aqueous medium. The depolymerizing reaction may be performed at any pH. Lower pH reactions favor higher yields of the phenolic compounds, while higher pH reactions favor higher yields of dicarboxylates. Peroxyacids are sometimes less stable at the highest pH ranges. In various non-limiting examples, the depolymerizing is performed in an aqueous solution at a pH of about 2 to about 4, about 2 to about 7, about 3.5 to about 10.5, about 7 to about 10.5, about 7 to about 12, and about 9 to about 11. Specific examples of pH values include about 2, about 3, about 4, about 5, about 6, about 7, about 8, about 9, about 10, about 11, and ranges between any two of these values (including endpoints).

The method may further include recovering phenolic compounds. The recovery may include an organic solvent extraction. The recovery may include a low temperature distillation. The recovery may include a steam distillation. The distillation may use reduced pressure and/or azeotropic distillations or similar distillations known to those of skill in the art. The recovered phenolic compounds may include vanillin, vanillic acid, gallic acid, or combinations thereof.

The method may further include substantial deoxygenating of the recovered phenolic compounds to give hydrocarbon fuel components. The deoxygenating may include substantial dehydration and hydrogenation of the recovered phenolic compounds to give hydrocarbon fuel components.

The method may further include recovering dicarboxylic acid compounds from a dicarboxylic acid fraction. The recovery may include extracting the dicarboxylic acid compounds into an aqueous solvent at a pH of about 3.5 or greater. In some embodiments, the extraction is into an aqueous mixture of about 3.5 pH to about 10.5 pH. The recovered dicarboxylic acid compounds may include muconic acid, succinic acid, maleic acid, or a combination thereof.

The method may further include esterifying the dicarboxylic acid fraction. The esterification may include formation of dialkyl esters, monoacid monoalkyl esters, and combinations thereof. In certain embodiments, the dialkyl esters may include a dialkyl muconate, a dialkyl succinate, a dialkyl maleate, or a combination thereof.

In various embodiments, the mixture of phenolic compounds is at least 28% total weight yield. In certain embodiments, the mixture of phenolic compounds is at least about 28%, about 35%, about 40%, about 45%, about 50%, about 55%, about 60%, about 70%, about 80% weight yield, or a weight yield between or including any two of the stated weight yields.

In various embodiments, the mixture of dicarboxylic acid and/or derivative ester compounds is at least 10% total weight yield. In certain embodiments, the mixture of carboxylate compounds is at least about 15%, about 20%, about 25%, about 30%, about 35%, about 40%, about 45%, about 50%, about 60% weight yield, or a weight yield between or including any two of the stated weight yields.

Other embodiments are an antimicrobial mixture of compounds. The mixture of compounds may include benzoic acid, vanillin, vanillic acid, gallic acid, and at least one substituted bisaryl ether. In some embodiments, the mixture is bactericidal at a concentration of 0.1 g/mL. In other embodiments, the mixture is bacteriostatic at a concentration of 0.01 g/mL.

In certain embodiments, the antibacterial agent may be produced by providing a lignin; decomposing the lignin with a peroxy acid for at least ten minutes and not greater than 3 hours at a temperature of not less than 40° C. to not greater than 120° C. to give the antibacterial agent. The antibacterial agent may be produced by providing a lignin; decomposing the lignin with a peroxy acid for at least ten minutes and not greater than 3 hours at a temperature of not less than 60° C. to not greater than 90° C. The antibacterial agent may be produced by decomposing a lignin with a peroxy acid, partitioning between aqueous phase and an organic phase, and further eluting the aqueous fraction through a chromatographic material. The chromatographic material may be a reverse-phase material. The antibacterial agent may be isolated. Isolation may include an organic solvent extraction. The isolation may include concentrating the antibacterial agent.

Other embodiments are an adhesive mixture of compounds. The adhesive mixture may be produced by providing a lignin; decomposing the lignin with a peroxy acid to give a decomposition product; partitioning the decomposition product between an aqueous phase and an organic phase; eluting the water fraction through a reverse-phase material with an acidic alkanol; and concentrating the adhesive product.

These technologies and embodiments illustrating the method and materials used may be further understood by reference to the following non-limiting examples.

EXAMPLES

Example 1: Depolymerization of Lignin

An alkaline lignin (Sigma) was treated by peracetic acid (PAA) at 60° C. The production of phenolic compounds from lignin was measured during 24 hours of reaction. As shown in FIG. 1, lignin was quickly depolymerized to low molecular weight phenolic compounds after peroxyacetic acid addition with a maximum phenolic compounds yield reached at approximately 62% following 1.5 hours of reaction. Extending the reaction time led to further disruption of the aromatic structure and formation of dicarboxylate compounds. The ratio between phenolic compounds and carboxylic acids depends on the lignin and reaction conditions. Varying the lignin source and reaction conditions, allowed yields of phenolic compounds of about 28% to 63% and carboxylic acids yield to about approximately 10% to 40%, as shown in FIG. 2.

Example 2: Depolymerization of Lignin to Form Phenolics

Dried lignin, 100 grams, having 80% contained lignin by Klason assay, is reacted with 15 grams of aqueous peracetic acid in 100 ml of hexane at a pH of about 4. Depolymerizing lignin in hexane led to an in-situ separation of polar and non-polar products in the respective water and hexane layers. The hexane layer contained mostly hydrocarbon compounds such as benzene and benzene derivative while the phenolic compounds were enriched enrich in the aqueous layer. The reaction is stopped at 1.5 hours at about 50° C. by cooling to room temperature and phase separation.

Figure 3:
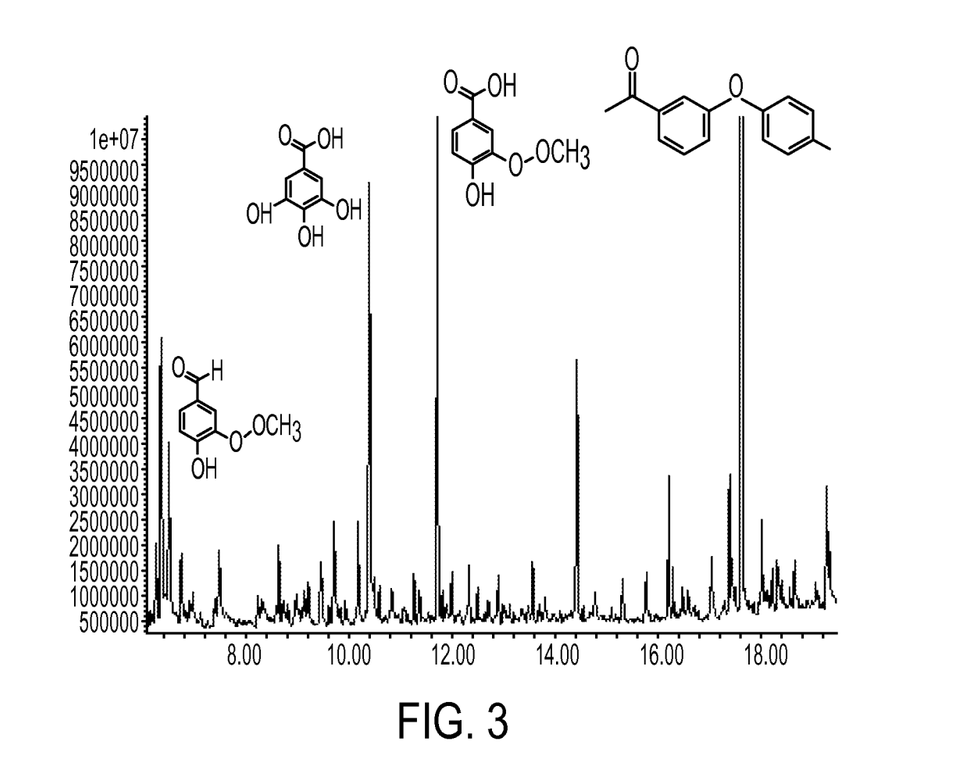
FIG. 3: Types of phenolic compounds identified by GC/MS analysis of silylated samples.

The phenolic compounds were isolated by HPLC and identified by GC/MS. The major phenolic constituents were vanillin, gallic acid, vanillic acid, benzoic acid, and phenolic dimers (FIG. 3). The weight yield of the phenols is about 65%.

The dicarboxylate compounds were identified in the aqueous fraction. The identified dicarboxylic acids included muconic acid, succinic acid, and maleic acid. These acids result from peroxy acid ring opening reactions. The weight yield of the dicarboxylates is about 10%.

Besides phenolic compounds and dicarboxylic acids, benzene, furan, and their derivatives are identified by GC/MS (5-15% weight yield). The benzene, furan, and derivatives are used or fuel components.

Example 3: Depolymerization of Lignin to Form Dicarboxylates

Peroxy acids depolymerization of lignin can be performed in aqueous media. 100 grams of dried lignin, having 50% contained lignin by Klason assay, is reacted with 25 grams of aqueous peracetic acid in water at a pH of about 9. The reaction is performed for 12 hours at about 80° C. The weight yield of the dicarboxylates is about 40%.

Example 4: Preparation of Polymer Precursors From Dicarboxylates

Besides achieving high phenolic compounds yield, oxidative depolymerization of lignin also provides a new pathway to convert lignin to aliphatic compounds for hydrocarbon fuel and polymer productions. The carboxylic acids of Example 3 are converted to polymer precursors. Hydrogenation (FIG. 4) of the dicarboxylate mixture converts muconic acid to the monomer adipic acid.

Example 5: Test of Antimicrobial Properties of Lignin Derivatives

Figure 5:
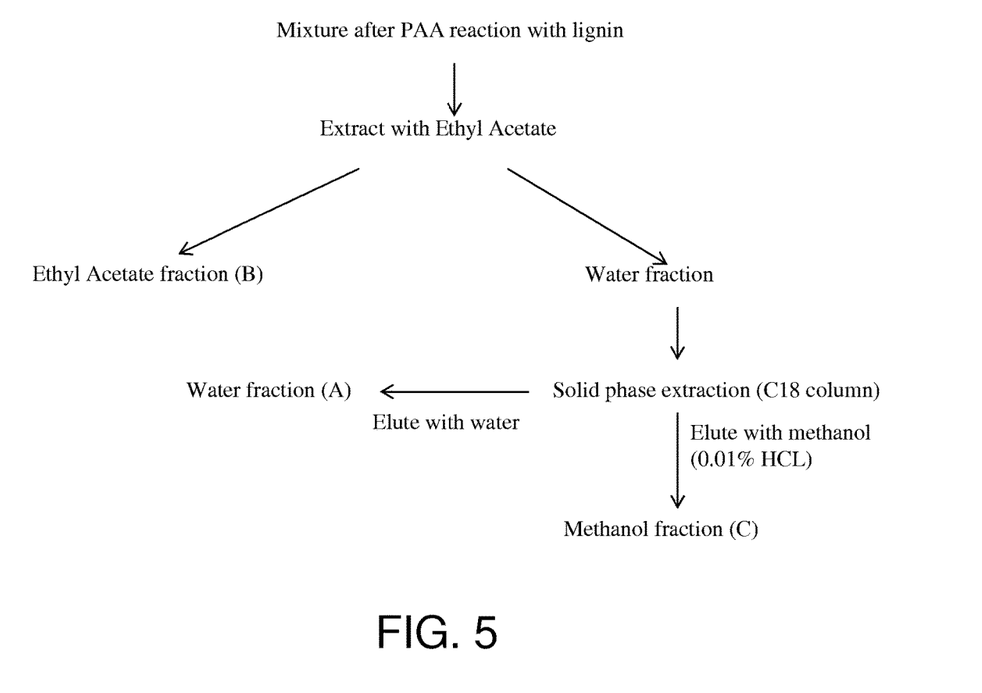
FIG. 5: A non-limiting example of a method to fractionation reaction mixture.
Figure 6:
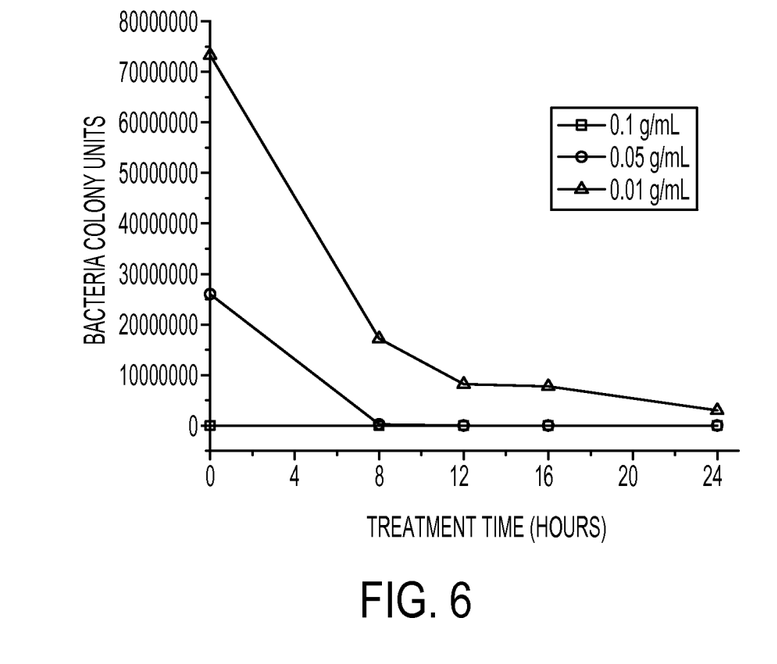
FIG. 6: The antibacterial activity of fraction B obtained from peroxyacetic acid depolymerization of alkaline lignin. Square symbols represent 0.1 g/mL, round symbols represent 0.05 g/mL, triangle symbols represent 0.01 g/mL.

The depolymerization reaction of Example 1 was extracted with ethyl acetate (see FIG. 5). The ethyl acetate fraction (B) was tested for antimicrobial effect (using *Salmonella enteritidis*) at 0.1 gm/mL, 005 gm/mL, and at 0.01 gm/mL. As shown in FIG. 6, the ethyl acetate fraction (B) was an effective antimicrobial agent. The ethyl acetate fraction inhibited the growth of *Salmonella* at a concentration of 0.1 g/ml. When the ethyl acetate fraction was used at a concentration of 0.05 g/ml it took between 8 and 12 hours to eliminate the bacteria. At a concentration of 0.01 g/ml the solution was a bacteriostatic agent, significantly reducing the number of bacteria colony units. Testing of the water fraction (A) showed similar antimicrobial effects as the ethyl acetate fraction (B).

Example 6: Test of Adhesive Properties of Lignin Derivatives

The various fractions of Example 1 (see FIG. 5) were tested for adhesive ability. Methanol Fraction C has shown good adhesive properties.

Figure 7:
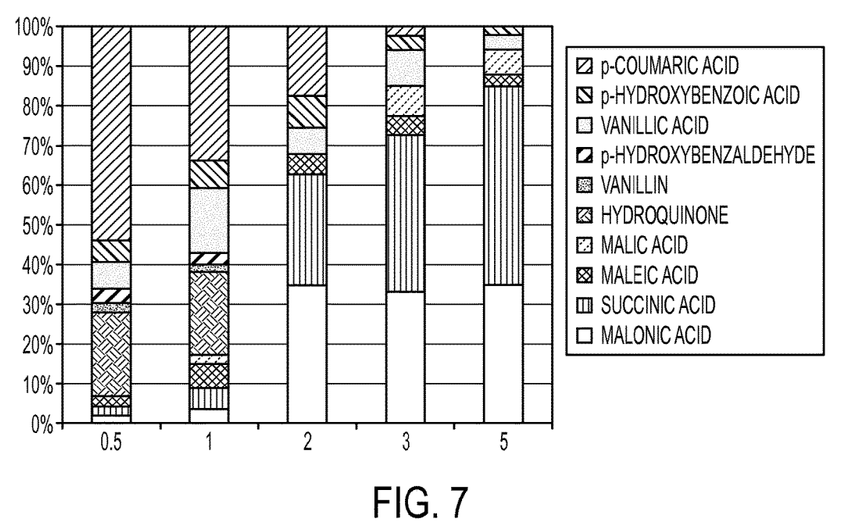
FIG. 7: A graph demonstrating conversion of an agriculture biomass lignin to phenolic compounds and dicarboxylic acids as a percent fraction of the total identified compounds. The graph is interpreted from bottom to top as: open boxes represent malonic acid, the vertical line boxes represent succinic acid, the diagonal square boxes represent maleic acid, dashed diagonal line boxes represent malic acid, diagonal brick boxes represent hydroquinone, heavier dot boxes represent vanillin, bold forward slash boxes represent para-hydroxybenzaldehyde, lighter dot boxes represent vanillic acid, back slash boxes represent parahydroxybenzoic acid, and forward slash boxes represent para-coumaric acid.

Example 7: Depolymerization of Lignin by In-Situ Produced Peroxyacid to Form Dicarboxylates An agricultural biomass lignin was depolymerized to phenolic compounds and dicarboxylic acids by a mixture of hydrogen peroxide and a transition metal catalyst, the ratios monitored by time as shown in FIG. 7. In the first half hour, phenolic compounds were the predominant compounds. Longer reaction time favors a higher yield of carboxylic acids.

Although the present technology has been described in considerable detail with reference to certain embodiments thereof, other versions are possible. Therefore, the spirit and scope of the appended claims are not be limited to the description and the versions contained within this specification.

What is claimed is:

1. A process comprising:
oxidatively depolymerizing a lignin with a peroxy acid at a temperature of not less than about 5° C. to not greater than about 160° C. to yield a mixture of dicarboxylic acid compounds and a mixture of phenolic compounds, wherein the mixture of dicarboxylic acid compounds is in at least about 10% total weight yield, wherein the total weight yield is calculated from the lignin on a contained lignin basis.

2. The process of claim 1, wherein the mixture of phenolic compounds is in at least about 28% the total weight yield.

3. The process of claim 1, further comprising:
substantially separating one or more dicarboxylic acid compounds or combination thereof from the mixture of phenolic compounds;
reducing at least one of the dicarboxylic acid compounds to a saturated dicarboxylic acid; and
recovering the one or more dicarboxylic acids or combination thereof in at least about 10% the total weight yield.

4. The process of claim 1, further comprising:
substantially separating one or more dicarboxylic acid compounds or combination thereof from the mixture of phenolic compounds;
esterifying at least one of the dicarboxylic acid compounds to a dicarboxylate ester; and
recovering one or more dicarboxylate esters or combination thereof in at least about 10% the total weight yield.

5. The process of claim 1, wherein the mixture of phenolic compounds is in at least about 60% the total weight yield.

6. The process of claim 1, wherein the mixture of dicarboxylic acid compounds is at least about 25% the total weight yield.

7. The process of claim 1, wherein the lignin is an alkaline lignin.

8. The process of claim 1, wherein the oxidatively depolymerizing the lignin with the peroxy acid comprises oxidatively depolymerizing at the temperature of not less than about 40° C. to not greater than about 120° C.

9. The process of claim 1, wherein the oxidatively depolymerizing the lignin with the peroxy acid comprises oxidatively depolymerizing for at least 3 hours.

10. The process of claim 1, wherein the peroxy acid comprises peracetic acid, performic acid, or combinations thereof.

11. The process of claim 1, wherein the peroxy acid is a peroxyaryloic acid.

12. The process of claim 1, wherein the peroxy acid is a peroxybenzoic acid.

13. The process of claim 1, wherein the peroxy acid is selected from the group consisting of metachloro-peroxybenzoic acid, peroxymonosulfuric acid, and peroxysulfonic acid.

14. The process of claim 1, wherein the peroxy acid is generated in-situ from an organic acid and hydrogen peroxide.

15. The process of claim 1, wherein the mixture of phenolic compounds comprises vanillin, vanillic acid, and gallic acid.

16. The process of claim 4, wherein recovering the one or more dicarboxylate esters comprises recovering a dicarboxylate ester fraction comprising a dialkyl muconate, a dialkyl succinate, a dialkyl maleate, or a combination thereof.

* * * * *

UNITED STATES PATENT AND TRADEMARK OFFICE
CERTIFICATE OF CORRECTION

PATENT NO. : 9,775,347 B2  
APPLICATION NO. : 14/898442  
DATED : October 3, 2017  
INVENTOR(S) : Zhang

Page 1 of 1

It is certified that error appears in the above-identified patent and that said Letters Patent is hereby corrected as shown below:

On the Title Page

In Item (71), under "Applicant", in Column 1, Lines 1-3, delete "WASHINGTON STATE UNIVERSITY RESEARCH FOUNDATION, Pullman, WA (US)" and insert -- WASHINGTON STATE UNIVERSITY, Pullman, WA (US) --, therefor.

Figure 4:
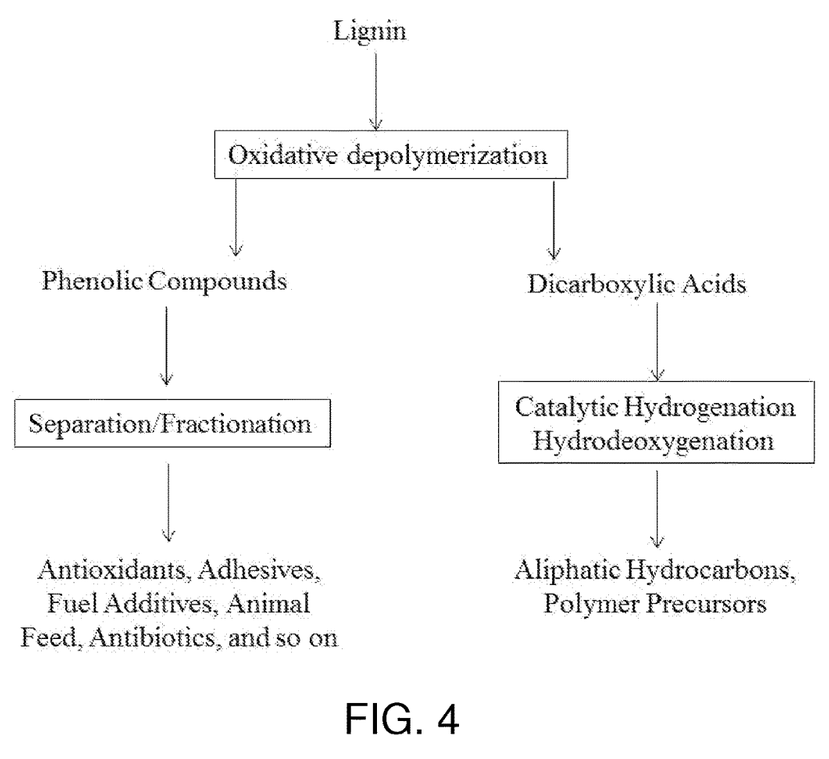
FIG. 4: Catalytic conversion of lignin to bioproducts and biofuel.

Insert FIG. 4, as the illustrative figure:

--.

Signed and Sealed this  
Twentieth Day of February, 2018

Andrei Iancu  
*Director of the United States Patent and Trademark Office*